US011974796B2

(12) United States Patent
Santoinanni et al.

(10) Patent No.: US 11,974,796 B2
(45) Date of Patent: May 7, 2024

(54) CATHETER FOR PLAQUE STABILISATION

(71) Applicant: Cryotherapeutics GmbH, Cologne (DE)

(72) Inventors: Domenic Santoinanni, Kirkland (CA); Stewart Maddison Fox, Cambridgeshire (GB); Daniel Nahon, Ottawa (CA); Peter Kyone Park, Milpitas, CA (US)

(73) Assignee: Cryotherapeutics GmbH, Cologne (DE)

( * ) Notice: Subject to any disclaimer, the term of this patent is extended or adjusted under 35 U.S.C. 154(b) by 188 days.

(21) Appl. No.: 15/028,790

(22) PCT Filed: Oct. 1, 2014

(86) PCT No.: PCT/EP2014/071098
§ 371 (c)(1),
(2) Date: Apr. 12, 2016

(87) PCT Pub. No.: WO2015/067414
PCT Pub. Date: May 14, 2015

(65) Prior Publication Data
US 2016/0249969 A1 Sep. 1, 2016

Related U.S. Application Data

(60) Provisional application No. 61/900,469, filed on Nov. 6, 2013.

(51) Int. Cl.
*A61B 18/02* (2006.01)
*A61B 18/00* (2006.01)

(52) U.S. Cl.
CPC .... *A61B 18/02* (2013.01); *A61B 2018/00023* (2013.01); *A61B 2018/00041* (2013.01);
(Continued)

(58) Field of Classification Search
CPC ............ A61B 18/02; A61B 2018/0212; A61B 2018/0262; A61B 2018/0268;
(Continued)

(56) References Cited

U.S. PATENT DOCUMENTS 5,417,689 A * 5/1995 Fine ...................... A61B 18/08
604/913
6,007,517 A * 12/1999 Anderson ........... A61M 25/104
604/103.04
(Continued)

FOREIGN PATENT DOCUMENTS

EP 1428478 A1 6/2004
EP 1430849 A1 6/2004
(Continued)

OTHER PUBLICATIONS

International Searching Authority—European Patent Office, International Search Report PCT/EP2014/071098, dated Jan. 9, 2015; 3 pages.

*Primary Examiner* — Sean W Collins
(74) *Attorney, Agent, or Firm* — Sunstein LLP

(57) ABSTRACT

Disclosed herein is a catheter for plaque stabilisation by cryotherapy, the catheter comprising: a first tube with a first end for receiving a flow of a coolant and a second end for supplying the flow of the coolant to a cooling element; a second tube, with a first end and a second end, wherein the second end of the second tube is configured to receive a flow of the coolant from the cooling element such that the second tube provides a flow path of the coolant from the second end of the second tube to the first end of the second tube; an inflatable flexible heat transfer element on the outer surface of the catheter; and a conduit for supplying an inflation fluid for inflating the flexible heat transfer element, wherein, when the flexible heat transfer element is inflated by the inflation fluid, the cooling element is configured to be within the balloon and in thermal conductivity with the inflation fluid; wherein the cooling element comprises an elongate tubular wall defining an elongate cooling chamber therein, the cooling chamber has a first end that is in fluid commu-
(Continued)

nication with the second end of the second tube and the cooling chamber has a second end that is closed.

23 Claims, 5 Drawing Sheets

(52) U.S. Cl.
CPC ........... *A61B 2018/00166* (2013.01); *A61B 2018/00214* (2013.01); *A61B 2018/0022* (2013.01); *A61B 2018/00791* (2013.01); *A61B 2018/00875* (2013.01); *A61B 2018/0212* (2013.01); *A61B 2018/0262* (2013.01); *A61B 2018/0268* (2013.01)

(58) Field of Classification Search
CPC .......... A61M 25/10; A61M 2025/1095; A61M 2025/1056; A61M 25/1025; A61M 2025/1097; A61F 7/123
See application file for complete search history.

(56) References Cited

U.S. PATENT DOCUMENTS

| | | | |
|---|---|---|---|
| 6,063,056 A * | 5/2000 | Engelberg | A61M 25/10 604/97.01 |
| 6,245,040 B1 * | 6/2001 | Inderbitzen | A61M 25/104 604/103.07 |
| 6,428,534 B1 | 8/2002 | Joye | |
| 6,468,297 B1 * | 10/2002 | Williams | A61B 18/02 607/105 |
| 6,908,462 B2 | 6/2005 | Joye et al. | |
| 6,989,009 B2 | 1/2006 | Lafountaine | |
| 2002/0007180 A1 * | 1/2002 | Wittenberger | A61B 18/02 606/21 |
| 2004/0116916 A1 * | 6/2004 | Lentz | A61B 18/02 606/21 |
| 2004/0116917 A1 * | 6/2004 | Lentz | A61B 18/02 606/21 |
| 2005/0228368 A1 | 10/2005 | Yon | |
| 2005/0288657 A1 * | 12/2005 | Lentz | A61B 18/02 606/23 |
| 2006/0015092 A1 | 1/2006 | Joye et al. | |
| 2006/0122589 A1 * | 6/2006 | Abboud | A61B 18/02 606/21 |
| 2011/0313410 A1 * | 12/2011 | Werneth | A61B 18/02 606/21 |
| 2012/0232543 A1 * | 9/2012 | Sharon | A61B 18/02 606/23 |

FOREIGN PATENT DOCUMENTS

| | | |
|---|---|---|
| JP | 2001-524345 A | 12/2001 |
| JP | 2004-188180 A | 7/2004 |
| JP | 2004-188181 A | 7/2004 |
| JP | 2005-523070 A | 8/2005 |
| JP | 2006-521878 A | 9/2006 |
| WO | WO 2002/069862 A1 | 9/2002 |

* cited by examiner

CATHETER FOR PLAQUE STABILISATION

BACKGROUND OF THE INVENTION

From the late 1970s, cryotherapy has been used in the cardiovascular system starting from, for example, 1977 when it was used to surgically treat cardiac arrhythmias. Over the ensuing years it became widely recognised that cryotherapy was particularly advantageous for working in the heart. Its safety and efficacy was unsurpassed as surgeons were able to ablate delicate cardiac structures such as the A-V node, pulmonary veins and delicate peri-nodal atrial tissue without concern for thrombosis, perforation or other adverse events.

More recently, researchers have started investigating the use of cryotherapy in the vascular system as a method to treat calcified plaque. Clinical data published by Laird et. al. "Cryoplasty for the Treatment of Femoropopliteal Arterial Disease: Extended Follow-up Results" J ENDOVASC THE 2006; 13 (Suppl II): II-52-II-59 has shown that cryotherapy achieves good clinical results when used in highly stenosed vessels of the peripheral vasculature.

Much of this previous work has been in treating calcified plaque in patients with calcified highly stenosed vessels (>70% stenosis) as an alternative to drugs, balloon angioplasty, stents or other conventionally used therapies.

Cryotherapy typically involves applying cooling to a vessel using a balloon based catheter, in which a refrigerant is used to expand a balloon into contact with a target. The temperatures used in treating such calcified highly stenosed blood vessels range from −10° C. to −20° C. (263K to 253K) and are generally warmer than those used in the ablation field (such as those used to treat arrhythmia or for cancer tumor ablation) where refrigerant temperatures will generally be colder than −70° C. (203K). Typically, the pressure in the balloon will be above 5 atmospheres (ATM), 507 kPa, as the goal of the therapy is to force open critically stenosed calcified vessels.

There has also been some interest in using cryotherapy on non-critically stenosed plaque typical of so called vulnerable or unstable plaque, as exemplified by U.S. Pat. Nos. 6,673,066, 6,602,246 and 6,955,174. Vulnerable plaque, or unstable plaque, may be defined as a non-flow limiting plaque which is lipid rich with a thin cap fibroatheroma. For the purposes of this document the terms vulnerable and unstable plaque are used interchangeably.

When these plaques rupture, a thrombus forms and causes a heart attack. A discussion, description and characteristics of these types of plaques is reviewed in Libby, "Atherosclerosis: The New View" Scientific American, May 2002, pg. 47. In some early work, the biological effect was poorly understood and improperly described as, for example, in U.S. Pat. No. 6,955,174 where cryotherapy treatment is described which "inhibits release of the retained fluid into the blood vessel". It is now thought that this mechanism is incorrect and that a ruptured plaque does not release materials into the bloodstream but causes a thrombus to form at the site of rupture. This mechanism is described by Muller, "Presentation at Cardiovascular Revascularization Therapies", Mar. 28-31, 2005, Washington D.C., and by Fuster et al, "Atherothrombosis and High Risk Plaque", Journal of the American College of Cardiology, 2005, Vol. 46, No. 6, pp. 937-54.

Many of the known cryocatheters have safety limitations. Typically, the catheter will use a phase change Joule Thomson refrigerant system in which liquid refrigerant transforms into a gas which inflates the catheter balloon. This system carries with it an inherent risk of gas leakage causing serious harm or death due to emboli. A typical device with such inherent risks is described in U.S. Pat. No. 6,908,462.

Additionally, the catheter in many devices employs a double balloon structure which causes an increase in bulk and diameter compared to smaller designs. The double balloon structure is used to place insulation between the balloons in order to achieve a correct target temperature, as is described in U.S. Pat. No. 6,514,255. A double balloon structure may also be used to mitigate safety concerns caused from gas leaks such as those described above. The increase in bulk and diameter makes the double balloon type design more difficult to develop a clinically acceptable design for small diameter arteries such as in the coronary or smaller peripheral vasculature where the catheter will be difficult to manoeuvre.

As described above, conventional cryotreatment for cardiovascular diseases has been aimed at cryoplasty, preventing restenosis of the vessel or treating atrial fibrillation. These methods typically use either a double walled balloon at a high pressure, usually to dilate the target vessel, or a solid, cooled probe tip to cause localized cryoablation.

There is a need to improve known catheter designs in order to provide effective cooling for treating unstable plaque that is likely to rupture, or has ruptured.

SUMMARY OF THE INVENTION

According to a first aspect of the invention, there is provided a catheter for plaque stabilisation by cryotherapy, the catheter comprising: a first tube with a first end for receiving a flow of a coolant and a second end for supplying the flow of the coolant to a cooling element; a second tube, with a first end and a second end, wherein the second end of the second tube is configured to receive a flow of the coolant from the cooling element such that the second tube provides a flow path of the coolant from the second end of the second tube to the first end of the second tube; an inflatable flexible heat transfer element on the outer surface of the catheter; and a conduit for supplying an inflation fluid for inflating the flexible heat transfer element, wherein, when the flexible heat transfer element is inflated by the inflation fluid, the cooling element is configured to be within the balloon and in thermal conductivity with the inflation fluid; wherein the cooling element comprises an elongate tubular wall defining an elongate cooling chamber therein, the cooling chamber has a first end that is in fluid communication with the second end of the second tube and the cooling chamber has a second end that is closed.

Preferably, the first and second tubes are coaxially arranged with each other such that, in a cross-section of the co-axial arrangement of the first and second tubes, the first tube is enclosed by the second tube.

Preferably, the cooling element is arranged co-linearly with the second end of the second tube.

Preferably, the conduit is further configured to provide a return flow of the inflation fluid of the flexible heat transfer element.

Preferably, the conduit comprises a third tube for providing a supply and/or return flow of the inflation fluid of the flexible heat transfer element; and the conduit comprises a fourth tube for providing a supply and/or return flow of the inflation fluid of the flexible heat transfer element.

Preferably, the catheter further comprises a restriction tube with a first end that is in fluid communication with the second end of the first tube and a second end for providing a flow of the coolant into the cooling chamber.

Preferably, the restriction tube has narrower internal diameter than the first tube.

Preferably, part or all of the cooling element is metal, such as copper, silver or gold.

Preferably, in a cross-section of the catheter, the flexible heat transfer element provides the entire outer surface of the catheter.

Preferably, the flexible heat transfer element is a balloon.

Preferably, in a cross-section of the catheter, the flexible heat transfer element provides part, but not all, of the outer surface of the catheter such that, when the catheter is inserted in a body and the flexible heat transfer element is inflated, blood can flow past the flexible heat transfer element.

Preferably, the flexible heat transfer element is a perfusion balloon.

Preferably, the catheter further comprises a guide wire lumen.

Preferably, the cooling element is not attached to the end of the guide wire lumen.

Preferably, the cooling element is configured such that, in use, the flow of the coolant causes the cooling element to vibrate.

Preferably, the restriction tube and cooling chamber are configured such that when the coolant is supplied to the first end of the first tube as a liquid, at least some of the coolant undergoes a phase change in the restriction tube and/or in the cooling chamber and returns through the second tube as a gas.

Preferably, the coolant is nitrous oxide.

Preferably, the catheter comprises a shaft for housing the tubes and conduit of the catheter.

Preferably, the shaft has an outer diameter in the range of 0.053" to 0.058".

Preferably, when the flexible heat transfer element is not inflated, the outer diameter of a part of catheter that comprises the flexible heat transfer element is substantially the same as the outer diameter of the shaft of the catheter.

Preferably, the second tube has the same outer diameter as the cooling element.

Preferably, the inflation fluid is an aqueous solution comprising a mixture of one or more of the following components: sodium chloride, calcium chloride, ammonia, ethanol, propylene glycol, ethylene glycol, propanone and butanone.

Preferably, the flexible heat transfer element has single walled outer membrane.

Preferably, the catheter further comprises means for heating the inflation fluid, or solidified inflation fluid, of the flexible heat transfer element.

Preferably, the means for heating is a resistor positioned inside the flexible heat transfer element but outside of the cooling element, such as a thin film resistor printed on the outer surface of the cooling element or a discrete resistor positioned inside the balloon.

Preferably, the means for heating comprises electrodes that apply an electric current directly to the inflation fluid.

According to a second aspect of the invention, there is provided a system for plaque stabilisation by cryotherapy, the system comprising: a catheter according to the first aspect of the invention; an inflation device configured to supply inflation fluid to the conduit in order to inflate the flexible heat transfer element; a coolant source configured to supply coolant to the first end of the first tube; and a vacuum pump configured to reduce the pressure in the second tube.

Preferably, the system further comprises: means for monitoring the pressure inside the inflated flexible heat transfer element; and means for determining if there has been any leakage of the inflation fluid from the catheter in dependence on the monitored pressure.

According to a third aspect of the invention, there is provided a method for plaque stabilisation by cryotherapy, the method comprising: supplying an inflation fluid to a catheter according to the first aspect of the invention to inflate the flexible heat transfer element of the catheter; supplying a coolant to the first end of the first tube of the catheter; and reducing the pressure in the second tube of the catheter.

Preferably, the method further comprises: monitoring the pressure inside the inflated flexible heat transfer element; and determining if there has been any leakage of the inflation fluid from the catheter in dependence on the monitored pressure.

According to a fourth aspect of the invention, there is provided a catheter for plaque stabilisation by cryotherapy, the catheter comprising: an elongate cooling chamber having a proximal end for receiving a coolant fluid and a distal end that is closed; a coolant supply lumen coupled to the cooling chamber for supplying a coolant fluid to the cooling chamber; an expandable member which encompasses the cooling chamber; and, an inflation lumen for supplying an inflation fluid for inflating the expandable member, wherein, in use, the inflation fluid provides a thermal pathway to conduct heat between a surface of the expandable membrane and the cooling chamber.

DETAILED DESCRIPTION OF THE DRAWINGS

Embodiments of the present invention will now be described in detail with reference to the accompanying drawings, in which.

DETAILED DESCRIPTION

Figure 1:
FIG. 1 shows a cross-section of a cooling element of a catheter according to an embodiment.

Embodiments of the invention provide an improved catheter device and system. Embodiments allow the cooling of vulnerable plaque that has ruptured, or is likely to rupture, at the surface of a blood vessel in order to modify the plaque structure, i.e. the plaque morphology will change from an unstable to a more stable state, such that healing is aided and the associated risk of thrombus formation is minimised or eliminated.

A brief description of a catheter design according to an embodiment is provided below.

The catheter has a balloon, one or more lumen for providing a supply and return of inflation fluid to the balloon and a cooling element for cooling the inflation fluid. The cooling element comprises tubular walls with a cylindrical cooling chamber therein. A co-axial arrangement of lumen provide supply and return paths of a coolant to and from the cooling chamber. The cooling element is elongate, linear and co-linear with, and of a similar diameter to, the outer of the lumen for the coolant. The cooling chamber is completely closed at the distal end to the connection to the supply and return lumen for the coolant such that these lumen provide the only inflow and outflow from the cooling chamber. The cooling of the cooling element is performed by at least some of the coolant undergoing a phase change. The one or more lumen that provide supply and return flows of a liquid for inflating the balloon are completely separate from the lumen used to supply the coolant. The inflation of the balloon and the cooling of the cooling element are performed by separate mechanisms and these operations can be controlled and operated independently of each other.

The catheter may also contain a means for heating the inflation fluid within the balloon. This would be used, for example, if the inflation fluid froze during treatment and it was necessary to rapidly thaw the inflation fluid. The ability to induce such rapid thawing is particularly beneficial in case the catheter needs to be removed from an artery quickly, for example in emergency situations. The heat could be provided by any type of heater, for example a small electric heater, such as a resistor, positioned inside the balloon but outside the cooling element and supplied by an electric current via wires running down the catheter shaft. The heater element could be formed by a thin film resistor printed on the outer surface of the cooling element, a discrete resistor positioned inside the balloon, or by the inflation fluid itself. In the case where the inflation fluid forms the heater element, wires would supply electricity to electrodes at the proximal and distal ends of the balloon and terminate there, in contact with the inflation fluid, so that an AC or DC current could be passed through the inflation fluid inside the balloon, causing it to warm up.

In use, the catheter is inserted into a body and positioned next to a region of unstable, or vulnerable, plaque in a vessel. The catheter's balloon is inflated by a liquid and the outer surface of the balloon comes into thermal contact with the plaque. Coolant is supplied to the cooling element and the temperature of the cooling element reduces. The inflation liquid within the balloon contacts the outer surface of the cooling element and is thereby cooled and may solidify. The inner surface of the balloon is thereby cooled by the liquid, that may have solidified, used to inflate the balloon and the outer surface of the balloon is thereby cooled. The balloon therefore removes heat from the plaque. The catheter can therefore be used to cool a target vessel having a suspected vulnerable plaque or other non-critically stenosed plaque typically of less than 70%. The vessel may be an artery or vein of any part of the body such as vessels of the heart, brain, kidneys, legs, arms or neck.

Preferably, the cryo-treatment is applied prior to the rupture of vulnerable plaque as a preventative measure. Alternatively, the cryo-treatment may be applied following a rupture to aid in stabilisation of the plaque to minimize the risk of event recurrence and to aid in healing. Cryo-treatment of the plaque causes the plaque morphology to change from an unstable to a more stable state such that healing is aided and a (re)occurrence of rupture and thrombus risk is reduced.

An advantageous aspect of the above-described catheter design is that the coolant of the cooling element is not the same as the fluid used to inflate the balloon. The cooling element can safely support a phase change of the coolant since the cooling chamber is closed. As the inflation fluid is a liquid, the requirement to have a double layered balloon is avoided even though the coolant may be a gas. A single layered balloon is significantly more manoeuvrable and streamlined than a balloon with multiple membranes. Moreover, the catheter design is simpler than known designs employing a double balloon system and this reduces costs and manufacturing complexity.

In addition the co-axial arrangement of the supply and return lumen for the coolant, as well as the elongate cooling chamber with a diameter similar to that of the outer lumen for the coolant, allow the cooling element and its supporting lumen to maintain a small cross-sectional area. This, together with not requiring a double layered balloon, allow the catheter to have a narrow diameter. The catheter is therefore suitable for applications in small diameter arteries, such as in the coronary or smaller peripheral vasculature, where known catheter designs are difficult to insert and/or manoeuvre.

In addition, cooling occurs, via the phase change, in the location where it is required. This improves the efficiency of the catheter system and the lumen that delivers the coolant does not need to have high levels of insulation between the coolant and the surrounding environment. Moreover, the co-axial arrangement of supply and return lumen means that the liquid coolant is kept cool by the cold, gaseous coolant returning from the distal tip of the catheter. This prevents the liquid coolant from boiling as it flows into that part of the catheter which is inside the body (and therefore at 37° C.).

Further advantages of embodiments are set out in the more detailed description of embodiments provided below.

FIG. 1 shows a cross-section of the design of a cooling element 105 according to an embodiment. On the left hand side of FIG. 1 are shown the tubular supply lumen 102 and the tubular return lumen 101 of the coolant. The return and supply lumen are co-axially arranged with each other, the supply lumen 102 being within the return lumen 101. An end of the supply lumen 102 is connected to and in fluid communication with a restriction tube 103. The restriction tube 103 has a narrower diameter than the supply lumen 102. The other end of the return lumen 101 to that connected to the supply lumen 102 ends in the cylindrical cooling chamber 104 of cooling element 105. In the present embodiment, the cooling chamber 104 has a slightly larger diameter than the return lumen 101. The cooling element 105 is an elongate linear tube that is closed at the distal end to the connection to the return lumen 101.

In use, a flow of pressurised coolant is input to the supply lumen 102. The coolant may be a liquid or a mixture of a liquid and a gaseous form of the coolant. The restriction tube 103 at the end of the supply lumen 102 ensures that there is little pressure drop with in the supply lumen 102 and so most, or all, of the pressurised liquid coolant remains in the liquid phase in the supply lumen 102. Along the length of the restriction tube 103, the pressure drops from a maximum value at the connection to the supply lumen 102 to a lower pressure at the exit of the restriction tube 103 into the cooling chamber 104. When the liquid coolant flows into the restriction tube 103 the pressure drop caused by the restriction means that the pressure of the liquid falls below its vapour pressure at the temperature of its surroundings at that point. This causes at least some of the liquid coolant to evaporate and undergo a phase change into a gas. Liquid coolant that flows from the restriction tube 103 into the cooling chamber 104 will also expand and may evaporate within the cooling chamber 104 and/or return lumen 101. The expansion of the coolant, and the phase change of the coolant, has a cooling effect on the cooling element 105. The coolant flows from the cooling chamber 104, in liquid and/or gaseous form, through the return lumen 101. The pressure within the return lumen 101, and thereby the cooling chamber 104, is preferably reduced by a vacuum pump. The vacuum pump, described in more detail later, operates on the other end of the return lumen 101 to that connected to the cooling element 105. The reduction of pressure both increases the cooling effect due to expansion and phase change of the coolant and ensures that the coolant in the cooling chamber 104 flows into the return lumen 101.

Figure 2:
FIG. 2 shows a cooling element of a catheter according to an embodiment.

FIG. 2 shows a perspective of the cooling element 105 of FIG. 1. Due to the co-axial arrangement of the supply and return lumen, it is the outer diameter of the return lumen 101 that defines the size of their cross-sectional area. The cooling element 105 has a slightly larger diameter than the return lumen 101. An advantage of having a slightly larger diameter of the cooling element 105 is that the cooling chamber 104 is larger and so there is more coolant, and phase change of the coolant, in the cooling chamber 104 and there is therefore a greater cooling effect. In addition, the outer diameter of the cooling element 105 has a lager surface area and is therefore more effective at cooling the inflation fluid. However, since it is also preferable to maintain a narrow catheter design for use in certain applications, the diameter of the cooling element 105 has only been increased by a small amount. An advantage of the cooling element 105 being linear and elongate is that a relatively large volume of cooling chamber 104 is provided with the cross-sectional area of the cooling chamber 104 being small. Increasing the volume of cooling chamber 104 can increase the cooling effect of the coolant.

The dimensions of the embodiment shown in FIGS. 1 and 2 are:
  Cooling element 105
    Outer diameter=0.032 to 0.041"; 0.8128 to 1.0414 mm
    Outer wall thickness=0.00075 to 0.002"; 0.0191 to 0.0508 mm
    Length=0.591 to 1.18"; 15 to 30 mm
  Return lumen 101
    Outer diameter=0.030"; 0.762 mm
    Outer wall thickness=0.00075 to 0.002"; 0.0191 to 0.0508 mm
    Length=39.4 to 68.9"; 1000 to 1750 mm
  Supply lumen 102
    Outer diameter=0.006 to 0.009"; 0.152 to 0.229 mm
    Outer wall thickness=0.00075 to 0.001"; 0.0191 to 0.0254 mm
    Length=39.4 to 68.9"; 1000 to 1750 mm
  Restriction tube 103
    Outer diameter=0.003 to 0.0055"; 0.0762 to 0.140 mm
    Outer wall thickness=0.00075 to 0.001"; 0.0191 to 0.0254 mm
    Length=0.5 to 2.0"; 12.7 to 50.8 mm Preferably the lumen and cooling element are made of reasonably strong and stiff materials so that they can withstand the pressure of a pressurised coolant. Preferably the lumen, and in some embodiments the cooling element, also have a degree of flexibility so that the catheter can deform to match the profile of an artery and the catheter have good 'trackability'.

The supply lumen 102, return lumen 101 and restriction tube 103 may be made of nylon, tri-layered tubing, polyimide, PEBAX™, such as PEBAX 55D, or other suitable materials. The restriction tube 103 and supply lumen 102 may be made at the same time so that they are integral with each other, or they may be constructed as separate components and then glued together. The cooling element 105 may be made of the same materials as said lumen but preferably the cooling element 105 is made entirely, or in part, of copper so that the cooling element 105 has good thermal conductivity properties.

Preferably, the coolant is $N_2O$ and enters the restriction tube 103 with substantially all of the coolant being in the liquid phase. The coolant may exit the restriction tube 103 with some of the $N_2O$ being in the liquid phase and some of the $N_2O$ being in the gas phase. Preferably, most of the $N_2O$ is in the liquid phase.

Figure 3:
FIG. 3 shows a cross-section of a cooling element of a catheter according to an embodiment.

An alternative embodiment of the cooling element is shown in FIG. 3.

The embodiment shown in FIG. 3 differs from that shown in FIG. 1 by the cooling chamber 301 of the cooling element 302 having the same inner and outer diameters as the return lumen 101. The cooling chamber 301 is still closed, i.e. blocked, at the other end to that connected to the return lumen 101.

The dimensions and materials of the return lumen 101, supply lumen 102 and restriction tube 103 may the same as described above with reference to the embodiments described in FIGS. 1 and 2. The length of the cooling chamber 301 from the end of the restriction tube 103 to the closed end of the cooling chamber 301 is preferably 1 mm to 15 mm.

Advantageously, the cooling element 302 is narrower than that shown in FIGS. 1 and 2. The cooling element 302 may be made at least in part of copper to ensure good thermal conductivity. Alternatively, the cooling element 302 may be made of the same material as the return lumen 101 as described above. This has the advantage of the cooling element 302 being easier to construct as the outer walls of the cooling chamber 301 can be the same as the walls of the return lumen 101.

Figure 4:
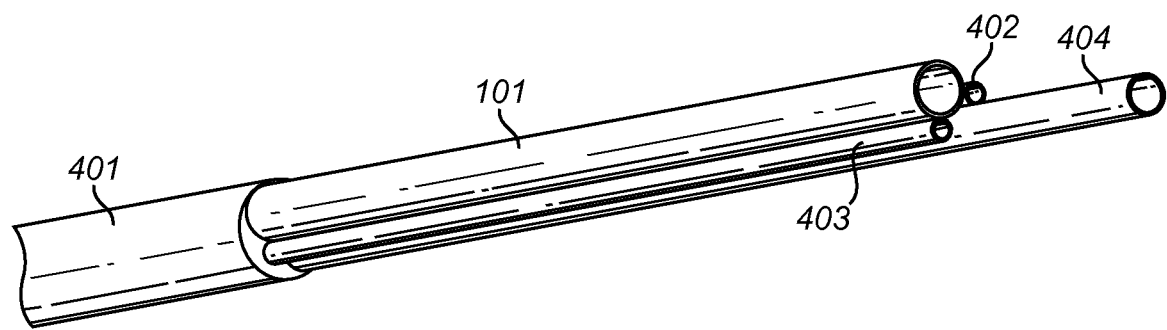
FIG. 4 shows cut-away representation of a shaft of a catheter according to an embodiment.

FIG. 4 is a cut-away representation of the components of a shaft 401 of a catheter according to an embodiment. The shaft 401 may be used to support any of the lumen and the cooling elements in the above-described embodiments.

In FIG. 4, in order to clearly show the components of the shaft 401, part of the outer sleeve has been cut-away, the full length of the lumen within the shaft 401 is not shown and the supply lumen 102 is not shown.

The shaft 401, comprises the return lumen 101, supply lumen 102 (not shown), guide wire lumen, GWL, 404 and lumen 402 and 403 for providing supply and return flows of inflation fluid. A sleeve is provided around all of the lumen. Preferably the sleeve is made of polyether block amide as braided, or unbraided, PEBAX™, such as PEBAX 55D, and is formed using a heat reflow process.

The lumen 402 and 403 are inflation and deflation lumen. The inflation and deflation lumen 402, 403 may be in fluid communication with each other at the proximal end, i.e. the other end to that shown in FIG. 4, so that fluid flowing through both of the lumen at the same time is used to inflate the balloon, and fluid flowing through both of the lumen at the same time is used to deflate the balloon.

Advantages of having two lumen to inflate and deflate the balloon include the supply and return of the inflation fluid being faster, better controlled and the overall cross sectional area of the sheath may be lower than if a single larger lumen is used for both supplying and providing a return flow of the inflation fluid.

The GWL 404 may be a standard angioplasty GWL which runs through a central lumen and a guide member which defines the tip of the catheter. As in known catheter systems, the system may be 'over the wire' or 'rapid exchange' as known in the art. The GWL 404 is preferably made of tri-layer or a similar material.

Figure 5:
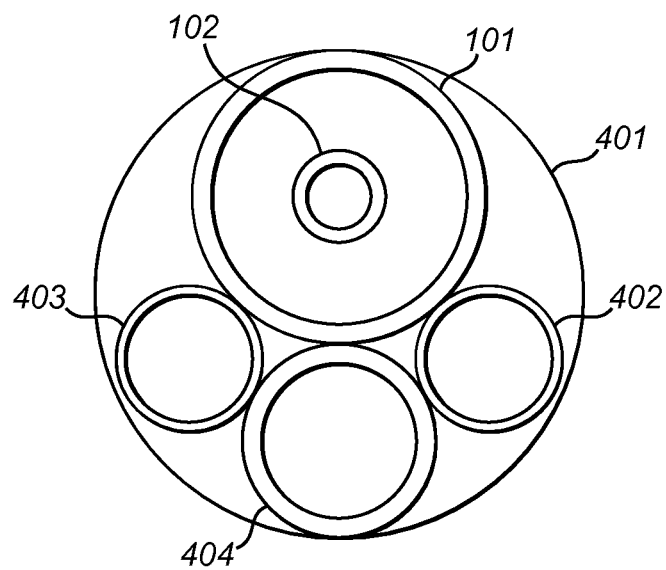
FIG. 5 shows a cross-section of a shaft of a catheter according to an embodiment.

FIG. 5 shows a cross-section of the shaft 401 of FIG. 4.

The co-axial arrangement of the supply lumen 102 inside the return lumen 101 is clearly shown.

The dimensions of the supply lumen 102 and the return lumen 101 are as provided in the above-described embodiments.

Figure 6:
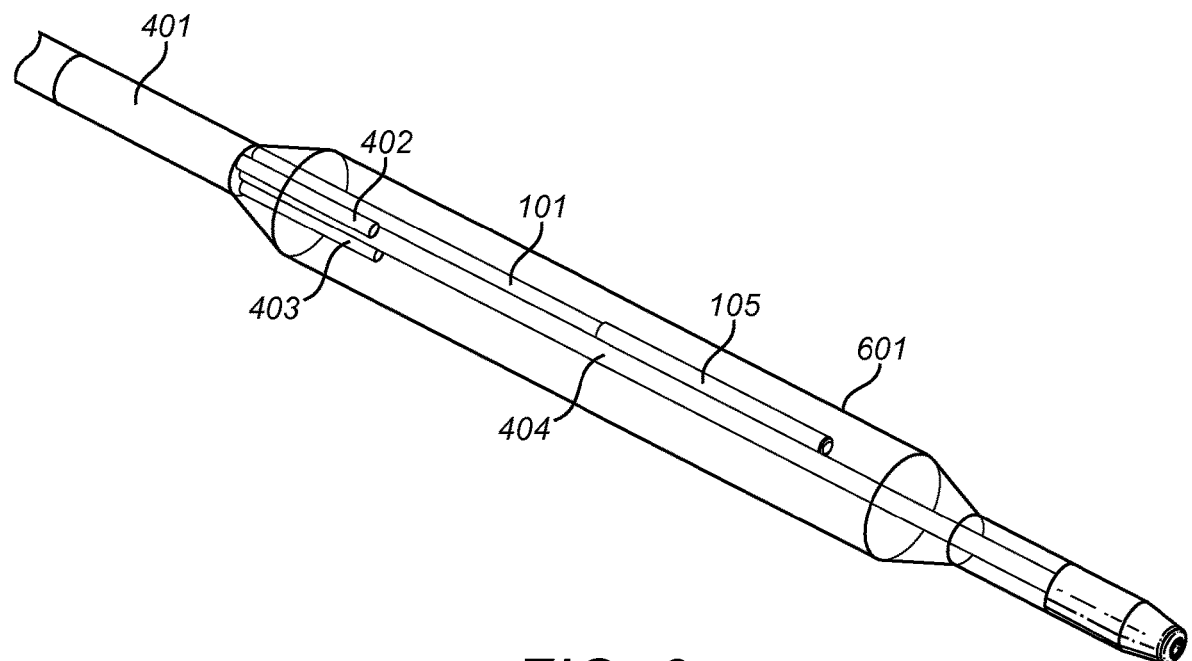
FIG. 6 shows an end of a catheter according to an embodiment.

The dimensions of the other components of the shaft 401 are:
  Inflation and deflation lumen 402, 403
    Outer diameter=0.010 to 0.016"; 0.254 to 0.406 mm
    Outer wall thickness=0.00075 to 0.002"; 0.0191 to 0.0508 mm
    Length=39.4 to 68.9"; 1000 to 1750 mm
  GWL 404
    Outer diameter=0.019 to 0.022"; 0.483 to 0.559 mm
    Inner diameter=0.016 to 0.019"; 0.406 to 0.483 mm
    Length=25.6"; 650 mm
  Shaft 401
    Diameter=0.053 to 0.058"; 1.35 to 1.47 mm The shaft 401 has a diameter of 4 Fr on the French gauge for catheter diameters. FIG. 6 shows the end of a catheter with the cooling element 105.

The end of the catheter shown in FIG. 6 comprises the cooling element 105 as described with reference to FIGS. 1 and 2 and the shaft 401, the inflation and deflation lumen 402, 403 and the GWL 404, as described with reference to FIG. 4.

The cooling element 105 is not attached to the end of the GWL 404 and the cooling element 105 is therefore free to vibrate, i.e. move laterally with respect to the longitudinal axis of the GWL 404. The end of the catheter as shown in FIG. 6 could alternatively have been constructed with the cooling element 302 as described with reference to FIG. 3. The cooling element 302 would also not be attached to the end of the GWL 404 in order for the cooling element 302 to be able to vibrate.

A balloon 601 is provided on the outer surface of the catheter. The balloon 601 extends round the entire outer surface of the catheter and, both when deflated and inflated (as shown in FIG. 6), has an elongate substantially cylindrical form. The cooling element 105 is encompassed by the balloon 601. That is to say, the cooling element 105 is within the inflation fluid of the balloon 601 and there is no outer membrane of the balloon 601 arranged between the inflation fluid and the cooling element 105.

The balloon is typically 15 mm to 30 mm long and, when deflated, is preferably substantially flush with the outer surface of the shaft 401 so that the outer diameter of the catheter is maintained substantially to 4 Fr. When inflated, the outer diameter of the balloon is preferably 2.5 mm to 4 mm.

The balloon may be made of a variety of materials and is desirably compliant or semi-compliant such that in use damage to the vulnerable plaque is minimised and to ensure a good fit with the target area for effective heat exchange and a more even temperature distribution around the plaque. The balloon may also be non-compliant if this is appropriate for the desired application. The balloon design and construction may be as known in the art of balloon angioplasty. However, there is no need for the balloons to be as strong, and with as thick membranes, as those used for angioplasty since the inflation pressures used in embodiments are substantially lower than those used in angioplasty. This is because the balloons are not required to enlarge the vessel. The balloons in embodiments are only required to make a good thermal contact with the vessel and the balloons are therefore preferably made with a thinner membrane than balloons used for angioplasty. The balloons can be made of a variety of materials such as silicone or polyurethane for compliant balloons and nylon or polyester for non-complaint balloons. Wall thickness will also vary depending on the properties to be achieved and are generally in the range of 5 to 100 microns (0.0002" to 0.004"). The balloon may also have a substantially smooth exterior surface so that heat transfer is optimised from the tissue on the interior surface of the vessel. The balloon material and thickness may be optimised to minimize the thermal gradient across the balloon surface.

In use, an inflation fluid is supplied to the inflation lumen 402 to inflate the balloon. The cooling element 105 is then cooled by the expansion and/or evaporation of the coolant as described in the above embodiments. The flow of the coolant, that may be a liquid and/or gas, from the restriction tube 103 into the cooling chamber 104 of the cooling element 105 causes the cooling element 105, which is not fixed to the end of the GWL 404, to vibrate. Advantageously, this vibration movement of the cooling element 105 increases the amount of flow of the inflation fluid over and around the cooling element 105 and thereby both increases the rate at which the inflation fluid is cooled by the cooling element 105 and the temperature uniformity of the inflation fluid. The inflation fluid is in contact with the inner surface of the balloon and the balloon is thereby cooled as the inflation fluid is cooled. The outer surface of the balloon is therefore cooled due to the cooling of the inflation fluid by the cooling element. When an operator determines that sufficient cooling has been applied by the catheter, the balloon is deflated using the deflation lumen 403 and the catheter can then be removed.

Preferably the inflation fluid has a fixed volume. This limits any damage caused by any leakage of the inflation fluid from the catheter. Any leakage of the inflation fluid can also be detected by monitoring the pressure of the inflation fluid when the balloon is inflated or by determining if the amount of inflation fluid after a procedure is the same as that at the start of the procedure.

The inflation fluid is preferably a liquid so that even if there is a leakage from the catheter, the leakage is of a liquid and not a gas. The inflation fluid may be a solution that comprises sodium chloride, such as saline, with a sodium chloride concentration of about 0.9%, or a solution with a higher concentration of sodium chloride, preferably a 25% concentration of sodium chloride. The inflation fluid is preferably water based, and may include various additives to lower the freezing point. Additives may include one or more of sodium chloride, calcium chloride, ammonia, ethanol, propylene glycol, ethylene glycol, propanone and butanone. Other additives may also be used.

The inflation fluid is preferably sterile. To ensure that the inflation fluid is sterile, the inflation fluid may be provided from a separate container, such as a pre-packed bag or syringe that is connected to the catheter.

The catheter could alternatively have been realised with the cooling element 105 fixed to the GWL 404. However, this would have prevented the cooling element 105 from vibrating and the cooling of the inflation fluid would have been slower.

Figure 7:
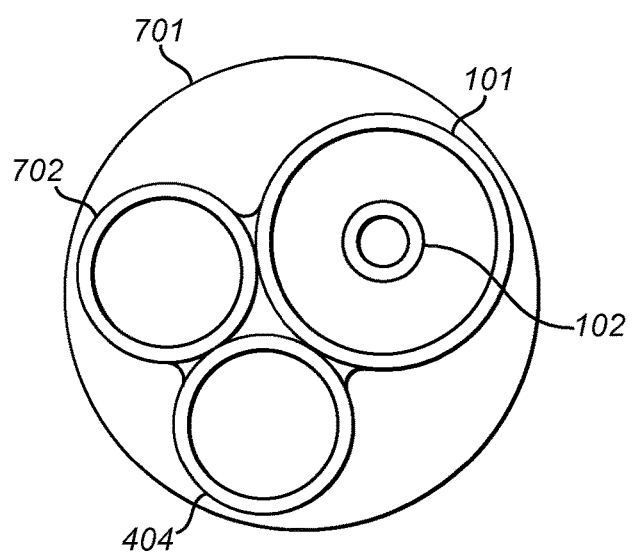
FIG. 7 shows a cross-section of a shaft of a catheter according to an embodiment.

FIG. 7 shows a cross-section of the shaft 701 of a catheter according to a further embodiment.

The shaft 701 differs from that shown in FIGS. 4 and 5 by having only a single lumen 702 for providing both the supply and return flows of the inflation fluid. The co-axial lumen for the coolant and the GWL 404 are as described in the above embodiments.

The same apparatus for supplying the inflation fluid to into the lumen may have its operation reversed so that it is also able to deflate the balloon by removing the inflation fluid. For example the inflation fluid may be injected into the lumen by an operator pressing on the plunger of a syringe. The same syringe can also be used to remove the inflation fluid by the operator withdrawing the plunger. Advantageously, such an arrangement allows an operator to easily determine if any of the inflation fluid has leaked from the catheter by checking how much inflation fluid is in the syringe after the balloon has been deflated.

Alternatively, separate apparatus for supplying and returning the inflation fluid may be provided.

A further advantage of having only a single lumen 702 for supplying and returning the inflation fluid is that the design of the catheter is simpler and the catheter is cheaper to manufacture.

The dimensions of the lumen 702 for providing both the supply and return flows of the inflation fluid are preferably:
  Inner diameter=0.017"
  Outer diameter=0.021"
  Length=100 cm-175 cm Preferably the lumen 702 is made of any of the materials as described above for the other lumen with reference to FIGS. 1 and 2 or a similar material. The diameter of the shaft 701 and material of the sheath may be the same as described above with reference to FIGS. 4 and 5.

Figure 8:
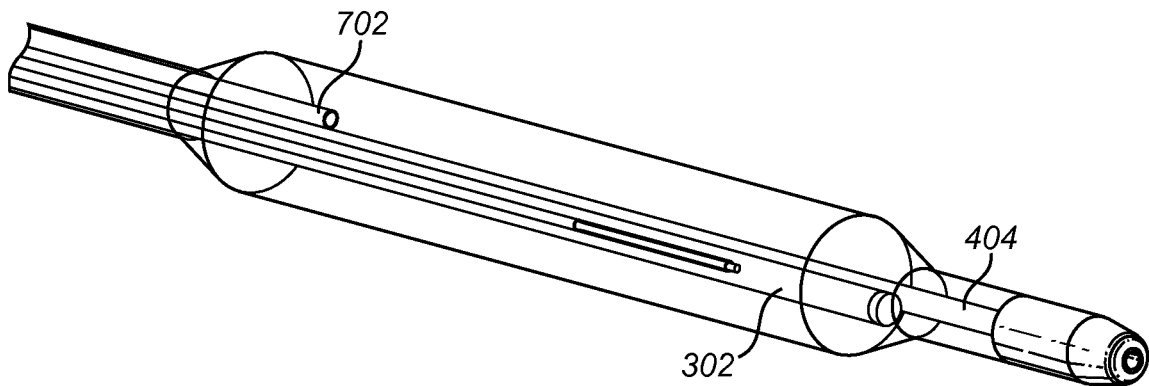
FIG. 8 shows an end of a catheter according to an embodiment.

FIG. 8 shows the end of a catheter supported by the shaft 701 shown in FIG. 7.

As well as having only a single lumen 702 for providing both the supply and return of the inflation fluid, the end of the catheter differs from that shown in FIG. 6 by having the cooling element 302 as described with reference to FIG. 3. The GWL 404 and balloon are as in the above-described embodiments.

The catheter is operated in the same way as that described with reference to FIG. 6, the only difference being the use of a single lumen for supplying and returning the inflation fluid. Preferably, the cooling element 302 is not fixed to the end of the GWL 404 so that the coolant causes it to vibrate.

Figure 9:
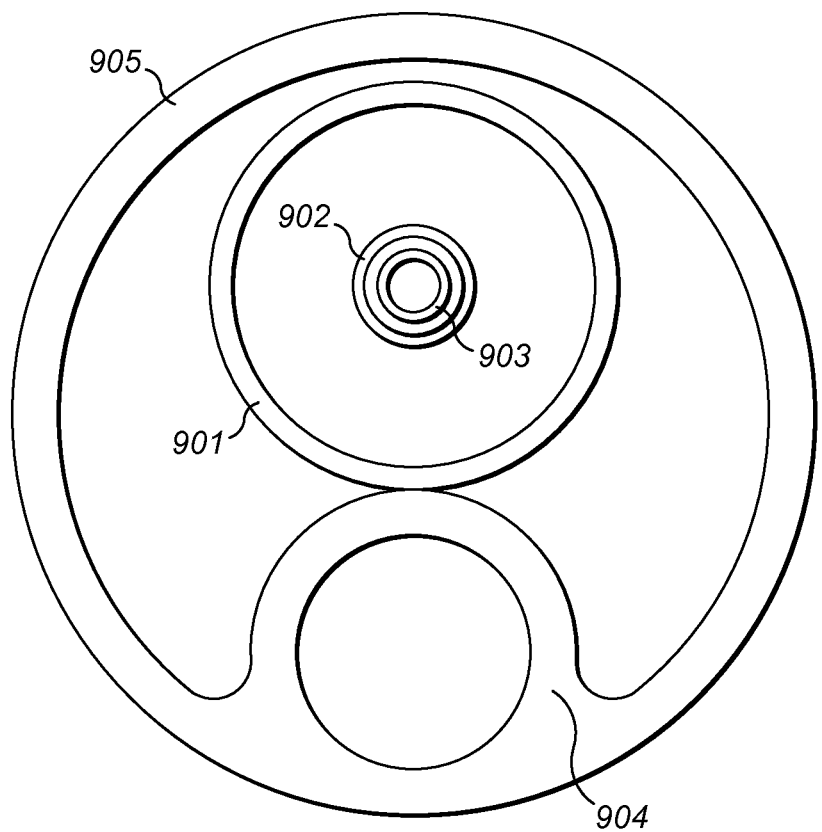
FIG. 9 shows a cross-section of a catheter according to an embodiment.

FIG. 9 is a cross-section of another catheter according to an embodiment. The catheter design differs from the above-described embodiments by the lumen for supplying the inflation fluid not having a cylindrical cross-section.

As in the above-described embodiments, the supply lumen 902 of the coolant is co-axially arranged within the return lumen 901 of the coolant and the restriction tube 903 is arranged at the end of the supply lumen 902. The GWL 904 is positioned next to the return lumen 901 in the catheter shaft 905.

The area shown in FIG. 9 that is within the shaft 905 and outside of the return lumen 901 and the GWL 904, is used to provide the supply and return flow of the inflation fluid. Advantageously, since the inflation fluid is not supplied through a lumen with a cylindrical cross-section, the space within shaft 905 is used more efficiently. The area within the shaft 905, outside of the return lumen 901 and the GWL 904, may also be used as a conduit for any electrical wires, such as wires for sensors or a heater.

Although not shown in FIG. 9, the catheter would also have a cooling element and balloon as described for any of the other catheters according to the embodiments described in the present document.

Preferable dimensions of the catheter shown in FIG. 9 are:
  Return lumen 901
    Outer diameter=0.029"; 0.74 mm
    Outer wall thickness=0.00157"; 0.04 mm
    Length=39.4 to 68.9"; 1000 to 1750 mm
  Supply lumen 902
    Outer diameter=0.00866"; 0.22 mm
    Outer wall thickness=0.000787"; 0.02 mm
    Length=39.4 to 68.9"; 1000 to 1750 mm
  Restriction tube 903
    Outer diameter=0.00512"; 0.13 mm
    Outer wall thickness=0.000591", 0.015 mm
    Length=0.5 to 2.0"; 12.7 to 50.8 mm
  GWL 904
    Outer diameter=0.023"; 0.59 mm
    Inner Diameter=0.017"; 0.43 mm
    Length=25.6"; 650 mm
  Shaft 905
    Outer diameter=0.057"; 1.45 mm
    Inner diameter=0.051"; 1.29 mm
    Outer wall thickness=0.0031"; 0.08 mm Alternatively, the return lumen 901, supply lumen 902, restriction tube 903 and GWL 904 of the present embodiment may be the same as the return lumen 101, supply lumen 102, restriction tube 103 and GWL 404 in the other embodiments described throughout the present document.

The component of the catheter may be made of the same materials as in the above-described embodiments.

Figure 10:
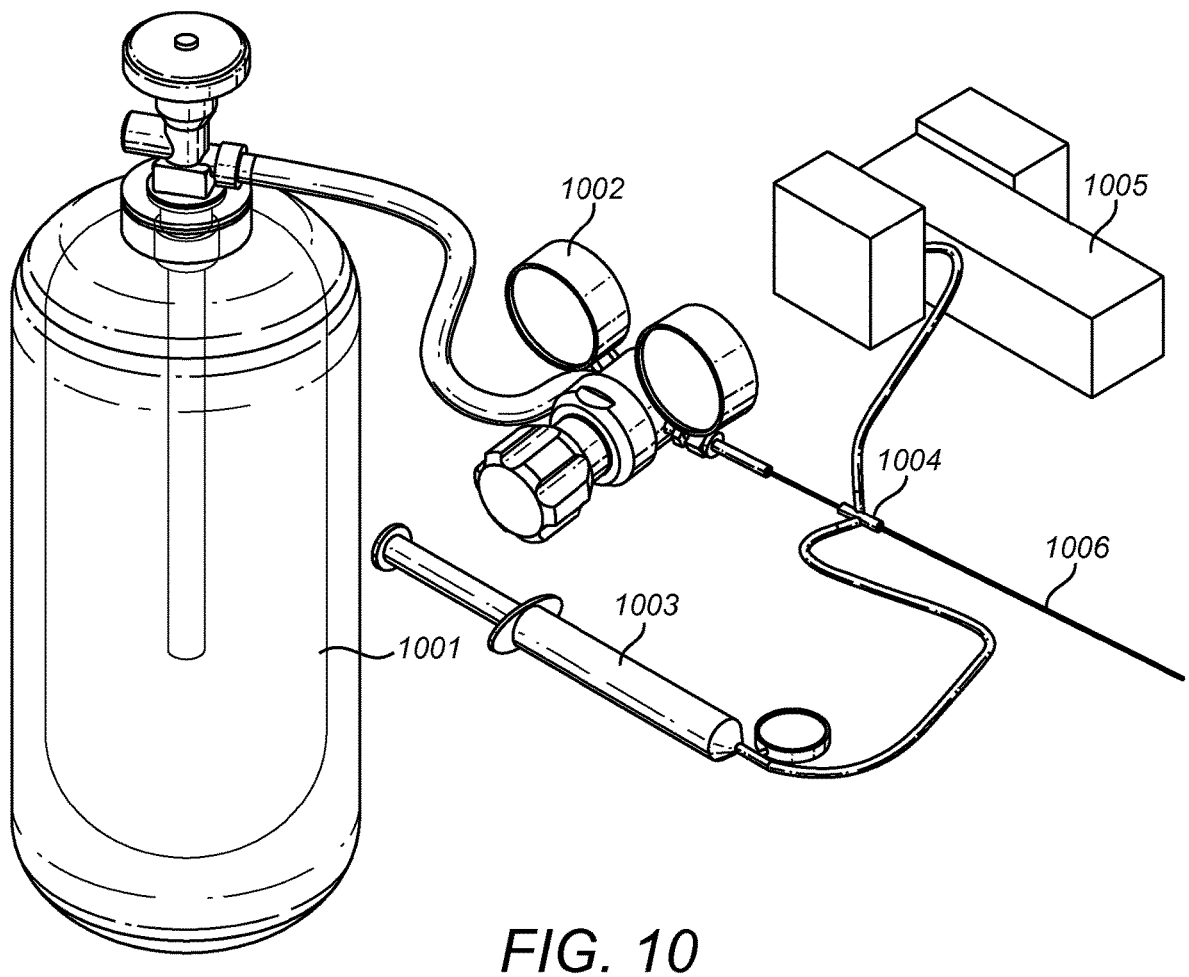
FIG. 10 shows a system for operating a catheter according to an embodiment.

FIG. 10 is an illustration of an exemplary system for using the catheter according to the embodiments described herein to cool a target part of a vessel. It will be understood that some of the specifically described components may not be essential to the operation of the system but are described for context only. Suitable, functionally similar, or equivalent components may be used interchangeably.

The system comprises:
  Coolant cylinder 1001
  Pressure regulator 1002
  Tri-connector 1004
  Vacuum pump 1005
  Inflation device 1003
  Catheter shaft 1006

Although not shown in FIG. 10, the system also comprises a catheter end according to any of the embodiments described herein.

The coolant cylinder 1001 has a dip tube and spigot valve for controlling the supply of the coolant. A flexible high pressure hose connects the coolant cylinder to the pressure regulator 1002. An injection tube from the pressure regulator connects to the tri-connector 1004. Also connected to the tri-connector is an inflation tube connected to inflation device 1003 and a vacuum tube connected to the vacuum pump 1005. The tri-connector maintains the injection tube, the vacuum tube and the inflation tube as separate from each other. The tri-connector also connects to the catheter shaft 1006 and thereby supports fluid and/or gas communication between the catheter and the coolant supply, vacuum pump, and inflation device.

The system may also include a heat exchanger, not shown in FIG. 10, to cool the liquid coolant before it enters the catheter. This will prevent boiling of the coolant as it enters the warm environment of the patient's body. Heat may be removed from the liquid coolant by using a refrigeration circuit or Peltier cooler.

The system may further comprise a computer, such that the system may be software controlled, the computer having one or more controls and/or a user interface such as a graphical user interface. The system may also further include assemblies for temperature and/or pressure monitoring based on signals received from one or more sensors.

The inflation device 1003 operates by causing an inflation fluid to flow into the catheter shaft 1006 when the plunger is pressed. The inflation device is also a deflation device since the inflation fluid flows back into the device from the catheter when the plunger is withdrawn. The inflation device may alternatively be an electric pump.

The vacuum pump 1005, that may be an electric vacuum pump, operates on the return lumen 101 of the coolant. The vacuum pump 1005 advantageously lowers the pressure in the cooling chamber 104, 301 of the cooling element 105, 302 to thereby increase the amount of phase change of the coolant that occurs. The vacuum pump 1005 also ensures that the coolant in the cooling chamber 104, 301 flows into the return lumen 101.

A further advantage applying the vacuum pump 1005 to the return lumen 101 is that the pressure in the return lumen 101 is relatively low and less than typical blood pressure in a body. In use, should the return lumen 101 leak, this would result in blood flowing into the return lumen 101 rather than the coolant flowing out. The vacuum pump 1005 thereby improves the safety of the catheter.

The catheter shaft 1006 in the system shown in FIG. 10 may be any of the catheter shafts 401, 701, 905 as described with reference to FIGS. 4, 5, 6, 7 and 9.

The system may also comprise a deflation device, separate from the inflation device 1003, that is in fluid communication with the catheter shaft 1006 through an additional separate connection to the tri-connector. The deflation device may be a vacuum pump, such as an electric vacuum pump.

Variables that influence the operation of the catheter are the pressure of the inflated balloon and the temperature of the outer surface of the balloon. Both of these are controllable by how the system of FIG. 10 is operated. The pressure of the balloon is controllable by controlling the amount, and pressure of, the inflation fluid by inflation device 1003. The temperature of the outer surface of the balloon is dependent on both the temperature of the cooling element 105, 302 and how long the cooling element 105, 302 has been cooling the inflation fluid. The temperature of the cooling element 105, 302 is controllable by controlling the pressure and the amount of coolant that flows into the catheter. The length of time that the inflation fluid is cooled by the cooling element 105, 302 is easily controlled by when the system operator starts the flow of the coolant into the catheter and removes the catheter.

Preferably, the pressure of the balloon is maintained at lower than 5 ATM (507 kPa) and may more preferably be as low as 3 ATM (304 kPa) or 1 ATM (101 kPa). It may be desirable for the balloon pressure to be as low as possible for effective treatment in order to mitigate the risk of a reaction occurring in the blood vessel that leads to re-stenosis or blockage. A short-term response to the application of high-pressure cryotherapy is also often smooth muscle cell proliferation, which is potentially dangerous. The tissue interface temperature is preferably maintained within a desired range in order to remove heat from the plaque and vessel without significantly ablating the cells. It is noted that throughout the present document, all pressures given as gauge pressures, that is, above atmospheric pressure.

The temperature of the outer surface of the balloon is preferably maintained between +15° C. (288K) and −35° C. (238K) and more preferably between 0 to −30° C. (273K to 243K). Depending on the type of balloon and the heat load, there may be a temperature difference of about 10° C. to 40° C. between inner and outer balloon temperature and this can be compensated for when controlling the system.

Preferably, sensors are provided within, on or near the catheter end, such as on or just inside the balloon, in order to monitor and thereby control the temperatures and pressures in a feedback control system. For example, a thermocouple may be fixed to the GWL 404 to measure the temperature inside the balloon. One or more further thermocouples may be attached to the internal or external surface of the balloon in order to measure the balloon tissue interface temperature. In addition, a pressure sensor may placed inside the balloon to accurately monitor and thereby control the pressure within the balloon. The pressure sensor may be an open hydraulic tube with no flow, or may be positioned on the inflation circuit near the inflator, so that the fluid pressure inside the tube is measured outside the catheter. The pressure sensor may also be a piezoelectric transducer, fibre-optic transducer or other type of sensor. Pressure sensors and a flow meter may also be positioned in the coolant circuit, to measure the pressure and flow of the coolant.

Both temperature and pressure signals can be used to control refrigerant flow such that balloon pressure and surface temperature remain within the desired ranges. The pressure transducer may also be used to detect any leaks within the catheter by sensing abnormal pressures. The temperature sensor(s) may also be used to detect vessel occlusion by the balloon.

As described earlier, the catheter may also comprise means for heating the inflation fluid, or solidified inflation fluid, within the balloon. Advantageously, this allows frozen inflation fluid to be thawed quickly if required.

In order to support the sensors, means for heating and any other devices at the distal end of the catheter, the system may further comprise connectors to one or more power supplies, data interfaces, or other signal processing units, configured to provide a power supply, control signals and to convert sensor signals into data. Electrical wires may be housed in the catheter shaft 401, 701, 905 together with the lumen or along the outside of the catheter shaft.

In use, the balloon may be expanded into thermal contact with the plaque for a limited period of time, such as less than 240 seconds or less than 180 seconds. In order to limit occlusion of the vessel the total time may be applied over multiple applications. Once the desired time has elapsed, the cooling is ceased. The balloon may be collapsed and the catheter removed from the vessel.

In an embodiment the catheter has a perfusion balloon instead of the type of balloon described with reference to FIG. 6. A perfusion balloon is designed to not completely block the flow of blood through a vessel during treatment and is therefore preferable if it is necessary to support extended treatment.

The pressure of the inflation fluid within the inflated balloon may also be used to detect if there has been any leakage of the inflation fluid. The pressure may be monitored over a period of time in order to detect if any drop in the pressure occurs, as this is indicative of there being a leak of the inflation fluid. The catheter may also be pressure tested in this way prior to being inserted into a body to further reduce the likelihood of a leak of the inflation fluid into the body occurring. Preferably, the volume of the inflation fluid is fixed and small. This minimises the damage caused by any leakage.

The injection of the inflation fluid to inflate the balloon may be automatically controlled and performed, for example, by an operator pressing a button. Alternatively, the inflation fluid may be injected manually.

Further embodiments include a number of modifications and variations that can be made to the embodiments as described above.

In particular, all of the dimensions provided in the figures are approximate and embodiments include catheter designs with different dimensions.

Throughout present document various features are described as lumen and tubes. These terms may be used interchangeably and said features may also referred to as conduits.

In the above-described embodiments, cooling elements are described as being preferably made entirely, or in part, of copper. Alternatively, the cooling element may be made entirely, or in part, of any metal, in particular silver, gold or any other material with good thermal conductivity properties.

In the above-described embodiments, the supply and return lumen 101, 102 of the coolant are described as being co-axially arranged with each other. Although this is a preferable feature, it is not essential and embodiments include catheter designs with supply and return lumen 101, 102 that are not coaxially arranged with each other. It is also not essential for the cooling element 105, 302 to be co-linear with the return lumen 101.

In FIG. 4, the inflation and deflation lumen 402, 403 may alternatively operate by one of the lumen only supplying a fluid for inflating the catheter balloon and the other lumen only providing a return path of the inflation fluid from the balloon.

The system may be configured such that a fixed amount of coolant is supplied to the catheter. This would limit any damage caused by any leaking of the coolant from the lumen 101 and 102 and the cooling chamber 104, 301. This may also allow any leaks of the coolant to be easily detected.

In the above described embodiments, the balloon is described as being inflated prior to the cooling element 105, 302 being cooled by the coolant. However, the cooling element 105, 302 could alternatively have been cooled by the coolant at the same time as, or prior to, the balloon being inflated.

Throughout the present document, embodiments of catheters are described as having balloons. However, the functionality of the described balloons is more generally provided by flexible heat transfer elements.

The embodiments described with reference to FIGS. 6 and 8 could alternatively have been implemented with different types of balloon, such as a perfusion balloon as described above.

Unstable plaque can occur in any region of the vasculature and the balloon sizing can therefore be varied for different applications. In embodiments, balloon diameters are preferably in the range of 2.0 mm to 4.0 mm however embodiments also include larger and smaller balloon diameters.

According to known techniques, one or more portions of the catheter 119 may be radiopaque and/or include a radiopaque marker. This aids the operator of the catheter.

In the above-described operation of the system, operational temperatures and pressures are provided. However, embodiments are in no way limited to these operational temperatures and pressures. Moreover, the operational temperatures and pressures may be varied depending on the application. In particular, embodiments include the catheter, and the system supporting the catheter, being operated according to the disclosure in WO2012/140439 A1, the entire contents of which are incorporated herein by reference.

A catheter according to the embodiments described throughout the present document is a catheter for plaque stabilisation by cryotherapy, the catheter comprising: an elongate cooling chamber having a proximal end for receiving a coolant fluid and a distal end that is closed; a coolant supply lumen coupled to the cooling chamber for supplying a coolant fluid to the cooling chamber; an expandable member which encompasses the cooling chamber; and, an inflation lumen for supplying an inflation fluid for inflating the expandable member, wherein, in use, the inflation fluid provides a thermal pathway to conduct heat between a surface of the expandable membrane and the cooling chamber.

Other embodiments of the invention will be apparent to those skilled in the art from consideration of the specification and practice of the embodiments disclosed herein. It is intended that the specification and examples be considered as exemplary only, with a true scope and spirit of the invention being indicated by the following claims. In addition, where this application has listed the steps of a method or procedure in a specific order, it may be possible, or even expedient in certain circumstances, to change the order in which some steps are performed, and it is intended that the particular steps of the method or procedure claims set forth herebelow not be construed as being order-specific unless such order specificity is expressly stated in the claim.

The invention claimed is:

1. A catheter for plaque stabilisation by cryotherapy, the catheter comprising:
    an inflatable flexible heat transfer element consisting of a single wall and having an exterior surface configured for exposure to a blood vessel into which the catheter has been inserted;
    an elongate tubular cooling chamber of substantially fixed volume disposed within the inflatable flexible heat transfer element;
    a coolant supply tube with a first end configured for receiving a flow of a coolant and a second end configured for supplying the flow of the coolant to the cooling chamber;
    a restriction tube, collinear with the coolant supply tube, with a first end that is in fluid communication with the second end of the coolant supply tube and a second end configured for providing a flow of the coolant into the cooling chamber;
    a coolant return tube having a first end and a second end and configured to receive a flow of the coolant from the cooling chamber along a flow path from the second end of the coolant return tube to the first end of the coolant return tube, wherein the coolant supply tube and the coolant return tube are coaxially arranged with each other such that, in a cross-section of the co-axial arrangement of the coolant supply tube and the coolant return tube, the coolant supply tube is enclosed by the coolant return tube;
    an inflation conduit having a port disposed within the inflatable flexible heat transfer element and configured for supplying a sterile inflation liquid for inflating the flexible heat transfer element so as to form a balloon, wherein, when the flexible heat transfer element is inflated by the inflation liquid, the cooling chamber is within the inflation liquid and thereby in direct thermal conductivity with the inflation liquid; and a guide wire lumen extending through the balloon along a path that is external to both of the coolant supply and coolant return tubes;

wherein the cooling chamber:
(i) has an interior cross sectional area larger than an exterior cross sectional area of the coolant supply tube and larger than an exterior cross sectional area of the coolant return tube,
(ii) has a first end that is in fluid communication with the second end of the coolant return tube,
(iii) has a second end that is closed; and
(iv) is configured such that when the coolant is supplied to the first end of the coolant supply tube as a liquid, at least some of the coolant undergoes a phase change in the cooling chamber, so as to cause cooling of the cooling chamber, and returns through the coolant return tube as a gas.

2. The catheter according to claim 1, wherein the cooling chamber is arranged co-linearly with the second end of the coolant return tube.

3. The catheter according to claim 1, wherein the inflation conduit is further configured to provide a return flow of the inflation liquid from the flexible heat transfer element.

4. The catheter according to claim 1, wherein the inflation conduit comprises a third tube configured for providing a supply flow of the inflation liquid to the flexible heat transfer element and a fourth tube configured for providing a return flow of the inflation liquid from the flexible heat transfer element.

5. The catheter according to claim 1, wherein the restriction tube has a narrower internal diameter than the coolant supply tube.

6. The catheter according to claim 1, wherein at least a part of the cooling chamber is made of a material selected from the group consisting of copper, silver and gold.

7. The catheter according to claim 1, wherein the flexible heat transfer element provides the entire outer surface of the catheter.

8. The catheter according to claim 1, wherein the cooling chamber is positioned within a central region, of the inflatable flexible heat transfer element, that is between a proximal end and a distal end of the inflatable flexible heat transfer element.

9. The catheter according to claim 1, wherein in a cross-section of the catheter, the flexible heat transfer element provides part, but not all, of the outer surface of the catheter such that, when the catheter is inserted in a blood vessel and the flexible heat transfer element is inflated, blood can flow past the flexible heat transfer element.

10. The catheter according to claim 9, wherein the flexible heat transfer element is a perfusion balloon.

11. The catheter according to claim 1, wherein the coolant is nitrous oxide.

12. The catheter according to claim 1, wherein the catheter further comprises a shaft for housing the coolant supply tube, the coolant return tube and the inflation conduit of the catheter.

13. The catheter according to claim 12, wherein the shaft has an outer diameter in the range of 0.053" to 0.058".

14. The catheter according to claim 12, wherein, when the flexible heat transfer element is not inflated, the outer diameter of a part of catheter that comprises the flexible heat transfer element is substantially the same as the outer diameter of the shaft of the catheter.

15. The catheter according to claim 1, wherein the inflation liquid is a solution comprising a composition selected from the group consisting of water, sodium chloride, calcium chloride, ammonia, ethanol, propylene glycol, ethylene glycol, propanone, butanone, and combinations thereof.

16. The catheter according to claim 1, further comprising means for heating the inflation liquid, or solidified inflation liquid, of the flexible heat transfer element.

17. The catheter according to claim 16, wherein the means for heating is a resistor positioned inside the flexible heat transfer element but outside of the cooling element.

18. The catheter according to claim 16, wherein the means for heating comprises electrodes configured to apply an electric current directly to the inflation liquid.

19. The catheter according to claim 1, wherein the cooling chamber is made from a first material that is different from a second material of the coolant return tube.

20. The catheter according to claim 1, wherein the second end of the coolant supply tube is part of a supply line extending beyond the second end of the coolant return tube and into the elongate cooling chamber.

21. A system for plaque stabilisation by cryotherapy, the system comprising:
a catheter according to claim 1;
an inflation device configured to supply inflation liquid to the inflation conduit in order to inflate the flexible heat transfer element;
a coolant source configured to supply coolant to the first end of the coolant supply tube; and
a vacuum pump configured to reduce the pressure in the coolant return tube.

22. A method for plaque stabilisation by cryotherapy, the method comprising:
supplying an inflation liquid to a catheter according to claim 1 to inflate the flexible heat transfer element of the catheter;
supplying a coolant to the first end of the coolant supply tube of the catheter; and
reducing the pressure in the coolant return tube of the catheter.

23. The method according to claim 22, further comprising:
monitoring the pressure inside the inflated flexible heat transfer element; and
determining if there has been any leakage of the inflation liquid from the catheter in dependence on the monitored pressure.

* * * * *